United States Patent [19]

Lysenko et al.

[11] Patent Number: 4,982,001

[45] Date of Patent: Jan. 1, 1991

[54] PROCESS FOR THE PREPARATION OF AMINO-1,3-BENZENEDIOL

[75] Inventors: Zenon Lysenko, Midland; Cynthia L. Rand, Sanford, both of Mich.

[73] Assignee: The Dow Chemical Company, Midland, Mich.

[21] Appl. No.: 290,068

[22] Filed: Dec. 27, 1988

Related U.S. Application Data

[62] Division of Ser. No. 110,754, Oct. 19, 1987.

[51] Int. Cl.$^5$ ................. C07C 213/02; C07C 215/80; C07C 201/08; C07C 205/00
[52] U.S. Cl. ............................ 564/418; 558/269; 568/706; 568/711
[58] Field of Search ............... 558/265, 269; 568/706, 568/711; 564/418

[56] References Cited

U.S. PATENT DOCUMENTS

| | | | |
|---|---|---|---|
| 2,370,588 | 2/1945 | Strain | 260/453 |
| 2,378,168 | 6/1945 | Witte | 260/585 |
| 2,379,250 | 6/1945 | Muskat et al. | 260/463 |
| 2,400,904 | 5/1946 | Batchelder et al. | 260/645 |
| 2,446,519 | 8/1948 | Bean | 260/575 |
| 2,458,214 | 1/1949 | Souders, Jr. | 260/580 |
| 2,517,965 | 8/1950 | Bohl | 260/463 |
| 2,525,515 | 10/1950 | Bean | 260/575 |
| 3,221,062 | 11/1965 | Wright | 260/622 |
| 3,933,923 | 1/1976 | Osberghaus et al. | 260/615 |
| 3,981,933 | 9/1976 | Cook et al. | 260/645 |
| 4,320,021 | 3/1982 | Lange | 252/51.5 R |
| 4,745,232 | 5/1988 | Schmitt et al. | 568/712 |
| 4,766,244 | 8/1988 | Lysenko | 564/418 |
| 4,788,346 | 11/1988 | Desbois | 568/706 |

FOREIGN PATENT DOCUMENTS 1009024  11/1965  United Kingdom .

OTHER PUBLICATIONS

Meyers et al., "Progress Toward the Total Synthesis of Maytansinoids, etc.", *Tetrahedron Letters*, No. 16, pp. 1375–1378, (1978).

*Primary Examiner*—Richard L. Raymond
*Assistant Examiner*—P. O'Sullivan

[57] ABSTRACT

High purity amino-1,3-benzenediols are prepared by (a) contacting a 1,3-bis(alkylcarbonato)benzene with a nitrating agent under reaction conditions such that a 1,3-bis(alkylcarbonato)nitrobenzene is formed, (b) contacting the 1,3-bis(alkylcarbonato)nitrobenzene with a hydrolyzing agent under conditions such that a nitro-1,3-benzenediol is produced, and (c) contacting the nitro-1,3-benzenediol with a reducing agent under conditions such that an amino-1,3-benzenediol is produced. Of the amino-1,3-benzenediols, 4,6-diamino-1,3-benzenediol is particularly useful in the preparation of high molecular weight polybenzoxazoles.

12 Claims, No Drawings

PROCESS FOR THE PREPARATION OF AMINO-1,3-BENZENEDIOL

This is a continuation of application Ser. No. 110,754, filed Oct. 19, 1987.

BACKGROUND OF THE INVENTION

This invention relates to a process for the preparation of amino-1,3-benzenediols and to novel intermediates used in their preparation.

Diaminobenzenediols and monoaminobenzenediols are useful as monomers for the preparation of polybenzoxazoles. Polybenzoxazoles can be prepared by reacting diaminodihydroxybenzenes with bisacids, bisacid halides, bisesters or bisnitriles. In order to obtain a high molecular weight polybenzoxazole which can be effectively spun into workable fibers, it is necessary that the starting materials used to form the polybenzoxazoles are of very high purity. Polybenzoxazoles prepared from highly pure diaminobenzenediols can be spun into fibers having high tensile strength and thermal stability. Such fibers are desirable for military, aerospace and other applications requiring high performance materials.

The traditional method for preparing 1,3-diamino-4,6-dihydroxybenzene involves the treatment of 1,3-diacetoxybenzene with white nitric acid. The treatment with nitric acid results in the formation of the undesirable 2,4,6-trinitro-1,3-benzenediol and 2,4-dinitro-1,3-benzenediol. Repeated recrystallizations are required to isolate the desired 4,6-dinitro-1,3-benzenediol from the undesirable by-products. The 4,6-dinitro-1,3-benzenediol is catalytically hydrogenated in dilute hydrochloric acid to produce the 4,6-diamino-1,3-benzenediol. See Wolfe et al., *Macromolecules*, 14, p. 909 (1981). This process is disadvantageous in that it requires extensive purification and utilizes expensive starting materials.

Monoamino benzenediols are known to be useful as materials for making dyes and are made by procedures similar to making diaminobenzenediols and which similarly suffer from the same deficiencies for making diaminobenzenediols.

What is needed is an economical high yield process which results in the formation of a substantially pure amino-1,3-benzenediol. Such a process would provide for the efficient production of amino-1,3-benzenediols which could be used to form the desirable high molecular weight polybenzoxazoles.

SUMMARY OF THE INVENTION

The present invention is such a process for the preparation of amino-1,3-benzenediols, particularly 4,6-diamino-1,3-benzenediols, 2-methyl-4,6-diamino-1,3-benzenediol and 4-amino-1,3-benzenediol, in high purity and yield. In one aspect, the process of the present invention comprises (a) contacting a 1,3-bis(alkylcarbonato)benzene with a nitrating agent under reaction conditions sufficient to form a 1,3-bis(alkylcarbonato)nitrobenzene, (b) contacting the 1,3-bis(alkylcarbonato)nitrobenzene with a hydrolyzing agent under conditions sufficient to form a nitro-1,3-benzenediol and (c) contacting the nitro-1,3-benzenediol with a reducing agent under conditions sufficient to form an amino-1,3-benzenediol. For the purposes of this invention, an "amino-1,3-benzenediol" is an aromatic diol having a benzene ring with a hydroxyl moiety in the 1- and 3-positions and at least one amino moiety substituted on the benzene ring.

It has been discovered that the practice of this aspect of the invention can yield 4,6-diamino-1,3-benzenediol of unusually high purity which can be utilized to prepare high molecular weight polybenzoxazoles. When desired, the practice of this aspect of the invention also can yield 4-amino-1,3-benzenediol in high purity which is useful as a monomer intermediate for the preparation of polybenzoxazole ethers.

In another aspect, this invention is a process for preparing a nitro-1,3-benzenediol which process comprises (a) contacting a 1,3-bis(alkylcarbonato)benzene with a nitrating agent under reaction conditions sufficient to form a 1,3-bis(alkylcarbonato)nitrobenzene and (b) contacting the 1,3-bis(alkylcarbonato)nitrobenzene with a hydrolyzing agent under conditions sufficient to form a nitro-1,3-benzenediol. Such nitro-1,3-benzenediols are useful as intermediates for making amino-1,3-benzenediols.

In a further aspect this invention is a 1,3-bis(alkylcarbonato)nitrobenzene such as formed as an intermediate in the aformentioned process.

DETAILED DESCRIPTION OF THE INVENTION

The 1,3-bis(alkylcarbonato)benzene employed as a starting material in the practice of this invention is advantageously one wherein alkyl has from 1 to 8 carbons, preferably from 1 to 4 carbons, most preferably methyl and represented by the structure

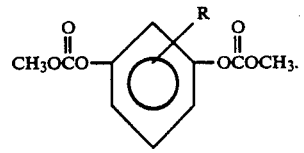

wherein R is hydrogen or alkyl having from 1 to 3 carbons, preferably methyl. The 1,3-bis(alkylcarbonato)benzene is advantageously prepared by contacting resorcinol with an alkyl haloformate under any conditions sufficient to form the desired 1,3-bis(alkylcarbonato)benzene. For example, suitable conditions for making the desired biscarbonates are described by Meyers et al. in *Tetrahedron Lett.*, 1375 (1978). Preferably, the desired biscarbonates are formed by adding an alkyl haloformate, most preferably methyl chloroformate, to a reactor containing resorcinol (1,3-dihydroxybenzene) and sodium hydroxide in a mixture of water and methylene chloride. The reaction mixture is preferably maintained at a temperature at or below 15° C.

The nitration step of the process of the present invention involves contacting a 1,3-bis(alkylcarbonato)benzene with a nitrating agent under conditions sufficient to form the corresponding 1,3-bis(alkylcarbonato)-4,6-dinitrobenzene. Any nitrating agent which will nitrate the 1,3-bis(alkylcarbonato)benzene at the 4 and 6 positions under the reaction conditions described herein can be utilized in the first step of the present invention. Suitable nitrating agents include alkali metal nitrates such as sodium and potassium nitrate and nitric acid at various concentrations, such as fuming nitric acid and concentrated nitric acid. Concentrated nitric acid, e.g., from about 60 to about 75 weight percent nitric acid, especially about 70 weight percent, is the most preferred nitrating agent.

Advantageously, the nitrating agent is employed in combination with an acid other than nitric acid. Any other acid which, in the presence of nitric acid, will facilitate the formation of nitronium ions under the reaction conditions described herein can be utilized in the first step of the present process. Preferred such other acids for this purpose include trifluoroacetic acid, hydrochloric acid and sulfuric acid, with hydrochloric acid being more preferred and sulfuric acid being most preferred.

Suitable molar ratios of the nitrating agent to the 1,3-bis(alkylcarbonato)benzene (hereinafter also referred to as the biscarbonate) are those sufficient to cause the substitution of 2 nitro groups on the benzene ring at the proportion of 2 nitro groups per molecule of the biscarbonate. Preferably, such ratios are those in the range from about 2:1 to about 3.3:1, with about 2.1:1 to about 2.8:1 being more preferred. The most preferred ratio is 2.5:1. The amount of the other acid used in the nitration step is advantageously any amount which will generate $NO_2 \oplus$ in sufficient concentration to fully dinitrate the biscarbonate. Preferred molar ratios of the other acid, preferably sulfuric acid, to the biscarbonate are in the range from about 9.5:1 to about 20:1, with about 10.5:1 to about 15:1 being more preferred. The most preferred ratio is 11:1.

The temperature of the nitration step can be any temperature at which nitration will occur. Preferred temperatures are in the range from about $-5°$ C. to about 90° C., with from about 0° C. to about 40° C. being more preferred. The pressure of the nitration step can be any pressure at which nitration will occur. Preferred pressures are about atmospheric, although subatmospheric or superatmospheric pressures can be employed.

The 1,3-bis(alkylcarbonato)nitrobenzene, which may have one or two nitro moieties, produced in the nitration step can be isolated by conventional precipitation and filtration techniques and is typically obtained in greater than about 80 percent purity, preferably greater than 85 percent purity and most preferably greater than about 90.5 percent purity. The product of the nitration step is typically obtained in yields greater than about 95 percent, preferably greater than about 97 percent and most preferably greater than about 99 percent based on the initial bis(carbonate). Upon removal of methylene chloride used in the nitration step, the 1,3-bis(alkylcarbonato)nitrobenzene can be immediately utilized in the hydrolysis step of the present invention without further purification.

The 1,3-bis(alkylcarbonato)nitrobenzene produced in this step is a novel compound and is represented by one of the formulae:

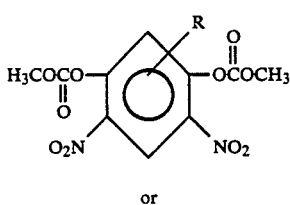

or

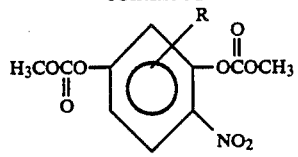

wherein R is hydrogen or alkyl or 1 to 3 carbons, preferably methyl.

The hydrolysis step of the present process involves contacting the 1,3-bis(alkylcarbonato)nitrobenzene prepared in the nitration step with a hydrolyzing agent under conditions sufficient to hydrolyze the carbonate moieties thereby forming hydroxyl moieties. Any hydrolyzing agent which will convert the carbonate moieties to hydroxyl moieties is suitable. Suitable hydrolyzing agents include alcohols such as lower alkanols, phenols, and mixtures of water and one or more alcohols or phenols. Examples of preferred lower alkanols include methanol, ethanol, propanol and butanol, with methanol and ethanol being more preferred and methanol being the most preferred. The hydrolysis step is advantageously carried out in the presence of an acid which will catalyze transesterification with the biscarbonate. Examples of acids which are advantageously employed in the hydrolysis step include hydrochloric acid, sulfuric acid, tetraalkoxytitanates and solutions thereof in sulfuric acid, with hydrochloric acid being the most preferred.

Suitable molar ratios of the hydrolyzing agent to the 1,3-bis(alkylcarbonato)nitrobenzene are those sufficient to hydrolyze both carbonate moieties. Examples of preferred ratios are those in the range from about 1000:1 to about 1:1, with about 20:1 to about 5:1 being more preferred. The most preferred ratio is 10:1. Preferred molar ratios of 1,3-bis((alkylcarbonato)nitrobenzene to acid are those sufficient to provide catalytic activity at a satisfactory rate. Examples of preferred molar ratios of 1,3-bis(alkylcarbonato)nitrobenzene to acid are those in the range from about 1:1 to about 100:1, with about 1:1 to about 10:1 being preferred. If base is employed instead of acid, a molar excess of base to starting material which is at least 4.5 or more is used. When acid is used as the catalyst, it is generally preferred to employ a tetraalkoxytitanate in combination with the acid. No additional catalyst is required when base is used as the catalyst.

The temperature of the hydrolysis step can be any temperature at which hydrolysis will occur. Preferred temperatures are in the range from about 20° C. to about 100° C., with from about 30° C. to about 70° C. being more preferred. The pressure used in the hydrolysis step can be any pressure at which hydrolysis will occur. Preferred pressures are generally about atmospheric, although subatmospheric and superatmospheric pressures can be suitably employed.

The product, e.g., 4,6-dinitro-1,3-benzenediol, of the hydrolysis step can be isolated by conventional precipitation and filtration techniques and is typically obtained in greater than about 95 weight percent purity, preferably greater than 97 weight percent purity and most preferably greater than about 99 weight percent purity. The product of the hydrolysis step is typically obtained in yields greater than about 85 mole percent, preferably greater than about 90 mole percent and most preferably greater than about 93 mole percent based on moles of hydrolysis starting material, e.g., 1,3-bis(alkylcarbonato)nitrobenzene, charged into the reaction. The nitro-1,3-benzenediol can be utilized as is in the reduction step of the present invention. Alternatively, it may be purified further by recrystallization from a suitable solvent such as methanol, propanol or ethyl acetate, with propanol being preferred.

The reduction step of the present invention advantageously involves contacting the nitro-1,3-benzenediol produced in the hydrolysis step with a reducing agent, preferably a hydrogenating agent, in the presence of a reduction catalyst, preferably a hydrogenation catalyst. The reduction step is preferably carried out in a solvent. The hydrogenating agent can be any material which will supply hydrogen to the reaction. Suitable hydrogenating agents include hydride reducing agents such as lithium aluminum hydride, stannous chloride in concentrated hydrochloric acid, dissolving metal reducing agents such as zinc metal and amalgams of sodium or cadmium, for example, and hydrogen gas. Of the hydrogenating agents, hydrogen gas is the most preferred.

The solvent which is preferably employed in the reduction step can be any solvent which will remain inert under reduction, preferably hydrogenation, conditions. Suitable solvents include alcohols such as ethanol, methanol and propanol, as well as alkylene glycols such as ethylene glycol and carboxylic acids such as acetic acid, with carboxylic acids being preferred. The most preferred solvent is propanol.

The hydrogenation catalyst can be any material which contains a noble metal and will catalyze the reduction of the nitro groups. Examples of suitable catalysts include noble metals on carbon, noble metal oxides and noble metals supported on alkaline earth carbonates. Noble metals herein refer to gold, silver, platinum, palladium, iridium, rhodium, mercury, ruthenium and osmium. Preferred catalysts include palladium-on-carbon, platinum-on-carbon and platinum oxide. The most preferred hydrogenation catalyst is 10 weight percent palladium-on-carbon. Preferred catalysts are those sold commercially as hydrogenation catalysts for the reduction or elimination of halogen from an aromatic.

The hydrogenation catalyst is employed in an amount which is sufficient to catalyze the conversion of starting material in the presence of a hydrogenating agent to the corresponding diaminobenzenediol. Typically, from about 0.001 to about 1 molar equivalents of catalyst are present per equivalent of nitro-1,3-benzenediol. Preferably, from about 0.01 to about 0.5 and most preferably from about 0.01 to about 0.1 equivalents of catalyst are present throughout the reaction.

When reduction is achieved by hydrogen reduction, the amount of hydrogenating agent employed in the reduction step is suitably an amount sufficient to convert all nitro moieties to amino moieties. Examples of such suitable amounts include those in the range from at least about 600 to about 2000 mole percent of reducing agent based on moles of nitro-1,3-benzenediol, preferably from about 610 to about 650 mole percent.

Alternatively to hydrogen reduction, the nitro-1,3-benzenediol can be reduced by contacting the nitro-1,3-benzenediol with a reducing agent such as stannous chloride dihydrate in a strong acid such as hydrochloric acid under reduction conditions. Other acids such as sulfuric acid can be substituted for hydrochloric acid. When using such a reduction procedure, the reducing agent is preferably employed in the range from about to about 8:1 to about 6.5, most preferably from about 7.5:1 to about 7:1 molar, equivalents of reducing agent per equivalent of nitrobenzenediol. The acid is preferably employed in an amount from about 100:1 to about 10:1, based on the amount of nitro moiety to be reduced.

Suitable concentrations of nitro-1,3-benzenediol in the reaction medium are those sufficient to afford an efficient recovery of product. Examples of such suitable concentrations are those in the range from about 0.001 to about 10 M (molar), with from about 0.1 to about 2 M being preferred. The most preferred concentration is 1 M.

The temperatures and pressures employed in the reduction step are sufficient to effect completion of the reduction. Preferably, the temperature is in the range from about 0° C. to about 150° C., most preferably from about 30° C. to about 75° C. Pressures employed are preferably from about atmospheric to about 300 psi, most preferably from about atmospheric to about 50 psi.

The amino-1,3-benzenediols can be recovered using known recovery methods such as precipitation and filtration. The product is generally isolated and stored as a hydrohalide salt in order to prevent oxidative decomposition. It is also suitable common practice to isolate the product as a salt of any mineral acid such as sulfuric, nitric or phosphoric acid. The amino-1,3-benzenediols produced in the practice of the present invention are typically obtained in a purity greater than 96 weight percent, preferably greater than 98 weight percent, most preferably greater than 99 weight percent, with yields being typically greater than 90 mole percent, preferably greater than 95 mole percent and most preferably greater than 96 mole percent, based on moles of 4,6-dinitro-1,3-benzenediol charged to the reaction.

SPECIFIC EMBODIMENTS

The following example is given to illustrate the invention and should not be construed as limiting the scope. All parts and percentages are by weight unless otherwise indicated.

EXAMPLE 1

A. Carbonation of Resorcinol

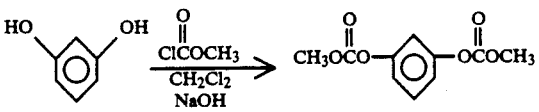

To a 5-liter, 3-necked, round-bottom flask equipped with a mechanical stirrer, condenser, thermometer and an addition funnel is charged while stirring, one liter of methylene chloride ($CH_2Cl_2$), one liter of a solution of 125 g of NaOH in water and 110 g (1 mole) of resorcinol. The resulting mixture is cooled to 0° C. and 250 ml (3.24 moles) of methyl chloroformate is added dropwise at a rate such that the temperature of the reaction mixture does not exceed 15° C. After 225 ml of the methyl chloroformate is added, an additional 300 ml of a solution of 5.0 g of NaOH in water and 10 ml of triethylamine is added to the reaction mixture while maintaining the temperature at 10° C. After this addition is completed, the remaining 25 ml of methyl chloroformate is added. The organic phase of the reaction mixture is washed with three (100-ml) portions of water and the methylene chloride phase which contains the reaction product is dried over $MgSO_4$ and then the methylene chloride is removed in vacuo to yield 220 g of 1,3-bis(- methylcarbonato)benzene which is suitable for use without further purification.

B. Nitration of 1,3-Bis(methylcarbonato)benzene

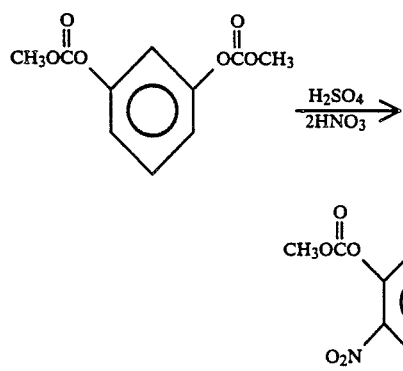

To a 5-liter, 3-necked, round-bottom flask equipped with a mechanical stirrer, condenser and addition funnel, is added 120 g (0.53 mole) of 1,3-bis(methylcarbonato)benzene in one liter of methylene chloride and cooled to 0° C. using a constant temperature bath. A solution of 136 ml of concentrated nitric acid and 136 ml of concentrated sulfuric acid is added dropwise to the flask with stirring at such a rate to maintain the temperature at 5° C. or below. Upon completion of the addition, the reaction mixture is heated to 25° C. and allowed to stir overnight. Analysis by gas chromatography shows conversion to mononitro-1,3-benzenediol (95 percent:5 percent 4-nitro isomer:2-nitro isomer, respectively). If a monoamine-1,3-benzenediol is desired, this product is then recovered and subjected to hydrolysis and reduction by the procedures set forth in Part C and Part D of this example.

The 1,3-bis(methylcarbonato)dinitrobenzene is formed by charging an additional 500 ml of concentrated sulfuric acid to the stirred reaction mixture containing the 1,3-bis(methylcarbonato)mononitrobenzene while maintaining the mixture at 25°·C. The temperature is allowed to rise to 40° C. and maintained at that temperature for 6 hours. The organic phase is separated and washed 3 times with 250-ml portions of water, dried over MgSO4 and evaporated in vacuo to yield 162 g of product consisting of 89 percent of 1,3-bis(methylcarbonato)-4,6-dinitrobenzene and 11 percent of 1,3-bis(-methylcarbonato)-2,4-dinitrobenzene. This material is used without further purification.

C. Hydrolysis of 1,3-Bis(methylcarbonato)nitrobenzene

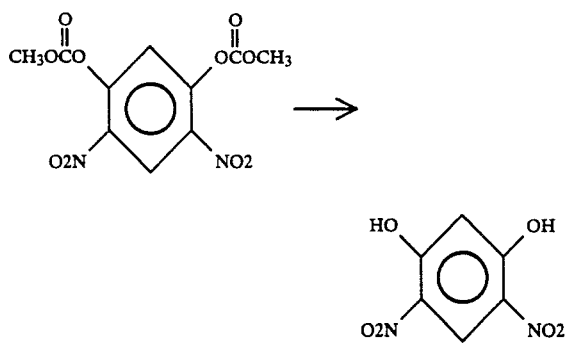

A 5-liter, 4-necked round-bottom flask is charged with 160 g (0.5 mole) of the product of Part B of this example dissolved in one liter of a mixture containing 400 ml of concentrated hydrochloric acid, 2 ml of tetrakis(n-butyl)titanate and a remaining amount of methanol. The reaction mixture is stirred at reflux (~67° C.) for 2½ hours. After such period, 100 ml of distilled water is added and the stirred reaction mixture is cooled to 6° C. The solid product which is formed is removed by filtration and dried in air to yield 87 g of 4,6-dinitro-1,3-benzenediol (98 percent yield based on the amount of 1,3-bis(methylcarbonato)-4,6-dinitrobenzene isomer charged at a purity of 98.7 percent).

D. Hydrogen Reduction of Nitro-1,3-benzenediol

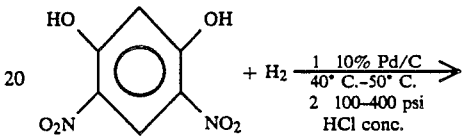

A one-liter Hastelloy C autoclave equipped with a gas dispersion stirrer and cooling coil is charged with 100.0 g (0.5 mole) of the 4,6-dinitro-1,3-benzenediol, 500 ml of n-propanol, ~7.0 g of 10 percent Pd/C and 10.0 ml of $H_2O$. The sealed reactor is charged with 50 psi of $H_2$ and the temperature is brought to 40° C. and maintained between 40° C.-50° C. during the course of the reaction. After a brief induction period, the uptake of hydrogen becomes extremely rapid and $H_2$ pressure is maintained at about atmospheric pressure during the reaction. Upon completion, no further uptake of $H_2$ is observed. The reactor is cooled to room temperature, opened and 300 ml of concentrated HCl containing ~10 g of $SnCl_2.2H_2O$ is added to the reaction mixture. The crude product with the catalyst is isolated by filtration. This material is dissolved in 200 g of $H_2O$ at 85° C. and the catalyst is removed by filtration. $H_2O$ (100-300 ml) is added to the filtrate along with 500 ml of HCl and the catalyst-free material is precipitated from the brown solution. Recrystallization may be carried out in the existing solvent or the semi-pure material can be isolated and air dried to afford 100 g of crude diamino resorcinol dihydrochloride (predominantly 4,6-diamino-1,3-benzenediol dihydrochloride in 95.0 mole percent yield based on the 4,6-dinitro-1,3benzenediol.

E. Recrystallization of Diamino Resorcinol Dihydrochloride (PBO Monomer)

A 100-g portion of crude product of Part D is added to 500 g of 3.5M HCl and heated until dissolved. A 10-g portion of decolorizing carbon and 2 g to 5 g of $SnCl_2.2H_2O$ are added and refluxing is continued for a period of 15 minutes. The carbon is removed by filtration and the recrystallizing solution is cooled to 0° C. The white needles are isolated by filtration under a $N_2$ blanket and dried to yield 85-95 g of the PBO monomer (due to the oxidative instability of this material it is recommended that recrystallization be carried out just prior to polymerization) (85 to 90 percent yield based on the product of Part D charged.

F. Polymerization of PBO Monomer

Generally following the procedures outlined in U.S. Pat. No. 4,533,693, a 100-ml resin kettle is loaded with 4,6-diamino resorcinol dihydrochloride (5.00 g, 23.4 mmole) obtained from Part E of this example, terephthaloyl chloride (4.76 g, 23.4 mmole) and polyphosphoric acid of 77 weight percent $P_2O_5$ (20.0 g). The polymerization is performed under nitrogen with stirring using the following profile: 40° C., 2 hours; 20° C., 120 hours; 40° C., 22 hours; 50° C., 24 hours; $+P_2O_5$ (10.3 g), 95° C., 24 hours; 150° C., 24 hours; 190° C., 24 hours. The resulting polymer solution exhibited stir-opalescence and readily formed fiber. Inherent viscosity=19.8 dl/g, in 25° C. methane sulfonic acid, c=0.05 g/dl.

EXAMPLE 2

A. Carbonation of Resorcinol

Into a 5-liter, 4-necked flask are charged 275 g of resorcinol, 1.5 liters of methylene chloride and a mixture of 625 g of 50 percent NaOH and 750 g of deionized water. After cooling to 0° C., 500 ml of methyl chloroformate is added dropwise at a rate sufficient to maintain the reaction temperature between 5° C. and 15° C. After addition is complete, a mixture of 250 g of 50 percent NaOH, 1250 g of deionized water and 20 ml of triethylamine is added. An additional 125 ml of methyl chloroformate is added and the mixture is heated to 25° C. and stirred for 20 minutes. The resulting creamy white mixture is allowed to separate into two phases and the organic phase is removed for use in the following nitration step.

B. Nitration

A 5-liter, 4-necked flask is charged with product obtained from part A and cooled to 0° C. To the flask is slowly added 2860 g of concentrated sulfuric acid, and thereafter 250 g of concentrated nitric acid is added dropwise at a rate sufficient to maintain the reaction temperature between 10° C. and 20° C. When the addition is complete, the reaction mixture is heated to 25° C. and mixed for 2 hours. The mixture is then cooled to 0° C. and 1000 ml of deionized water is added dropwise at a rate sufficient to keep the reaction temperature at 10° C.-20° C. The reaction mixture is then allowed to separate into phases. The organic phase is withdrawn and subjected to vacuum to remove the solvent thereby yielding 821 g of a light yellow powder. The powder is determined by nuclear magnetic resonance to be predominantly (95 percent) 4-nitro-1,3-bis(methylcarbonato)benzene.

C. Decarbonation

The 5-liter, 4-necked flask is charged with 410 g of the nitration product of part B dissolved in 500 ml of methanol and cooled to 15° C. while adding 1200 ml of deionized water. When the reaction mixture is cooled to 15° C., a mixture of 700 g of 50 percent NaOH and 300 g of deionized water is added. After stirring the reaction mixture for one hour at 25° C., the temperature is increased to 44° C. and 25 g of 50 percent NaOH is added. The mixture is then heated to 56° C. for 3 hours, cooled to 0° C. and 100 ml of concentrated HCl is added dropwise. The resulting yellow precipitate is removed by filtration and washed repeatedly with deionized water to yield 180 g of wet powder (4-nitro-1,3-benzenediol). The remaining half of the 821 g of the product of part B is similarly treated and recovered to provide 145 g of yellow powder.

D. Reduction

Into a 5-liter, 3-necked flask is charged 180 g of the wet powder product of part C dissolved in 3 liters of n-propanol. After addition of a palladium-on-carbon catalyst (5 g of 58 percent dispersion of catalyst in water), hydrogen gas is bubbled into the reaction mixture producing an exotherm and a color change from green to red to black. As the reaction mixture turns black, the hydrogen uptake and exotherm ceases and the reaction mixture is cooled to 25° C. A 10-g portion of stannous chloride dihydrate dissolved in 750 g of concentrated HCl is added. The catalyst is removed by filtration and the solvent is removed in vacuo to yield a gray cake (125 g dry). The 145-g portion recovered in the second procedure of part C is similarly treated and produces 112 g of gray cake. The gray cake is recrystallized by dissolving 125 g of the cake in 190 g of concentrated HCl containing 5 g of stannous chloride dihydrate and 2 g of activated carbon and heating the mixture to 100° C. for 15 minutes. The mixture is filtered and the resulting supernatant is cooled to 0° C. and filtered to remove a white precipitate (110.2 g after drying in a vacuum oven). Nuclear magnetic resonance analysis of the white precipitate indicates it to be 4-amino-1,3-benzenediol. Yield of the final product based on the amount of resorcinol (1,3-benzenediol) is 65 percent overall.

EXAMPLE 3

Preparation Of 2-Methyl-4,6-Diamino-1,3-Benzenediol

Following the procedure of Example 2, 2-methyl-1,3-benzenediol is converted to 2-methyl-4,6-diamino-1,3-benzenediol in a yield of 75 percent.

EXAMPLE 4

Methyl cis PBO Homopolymer

In an inert environment, 2-methyl-4,6-diamino-1,3-benzenediol dihydrochloride (6.80 g, 29.9 mmoles), terephthaloyl chloride (6.08 g, 29.9 mmoles), and polyphosphoric acid (28.6 g having 76.7 percent $P_2O_5$) are loaded into a 100-ml resin kettle. Reaction is performed under nitrogen with mixture mechanically stirred and warmed with an oil bath to the following reaction profile: 40° C., 16 hours; 50° C., 24 hours; 95° C., $+P_2O_5$ (15.9 g), 24 hours; 135° C., 24 hours; 190° C., 24 hours. At the end of the reaction, the mixture exhibits increased viscosity and can be formed into fibers. Inherent viscosity of the resultant polymer is 17.6 dL/g in methanesulfonic acid at a concentration of 0.05 g/dL and a temperature of 25° C. Upon heating the polymer in air at a heating rate of 20° C./min, degradation occurs at 621° C.

EXAMPLE 5

Methyl cis PBO Copolymer

In an inert environment, 2-methyl-4,6-diamino-1,3-benzenediol dihydrochloride (1.71 g, 7.51 mmoles), 4,6-diamino-1,3-benzenediol dihydrochloride (8.00 g, 37.6 mmoles), terephthaloyl chloride (9.15 g, 45.1 mmoles), and polyphosphoric acid (40.2 g) having a phosphorous pentoxide content of 76.4 percent are loaded into a 10-ml resin kettle. Reaction is performed under nitrogen while stirring and heating the reaction according to the following profile: 40° C., 16 hours; 50° C., 24 hours; 95° C., +P$_2$O$_5$ (23.5 g), 24 hours; 150° C., 24 hours; 190° C., 24 hours. At the end of the reaction, the reaction mixture exhibits increased viscosity and can be formed into fibers. Inherent viscosity of the copolymer is 15.9 dL/g in methanesulfonic acid at a concentration of 0.05 g/dL and 25 C.

What is claimed is:

1. A process for the preparation of amino-1,3-benzenediol in high purity comprising the steps of
   (a) contacting a 1,3-bis(alkylcarbonato)benzene with a nitrating agent under reaction conditions sufficient to form a 1,3-bis(alkylcarbonato)-nitrobenzene in a yield of at least 95 weight percent based on the weight of the 1,3-bis(alkylcarbonato)benzene;
   (b) contacting the 1,3-bis(alkylcarbonato)nitrobenzene with a hydrolyzing agent under conditions sufficient to form a nitro-1,3-benzenediol; and
   (c) contacting the nitro-1,3-benzenediol with a reducing agent under conditions sufficient to form an amino-1,3-benzenediol.

2. The process of claim 1 wherein the 1,3-bis(alkylcarbonato)benzene is 1,3-bis(methylcarbonato)benzene.

3. The process of claim 1 wherein the nitrating agent is nitric acid, and sulfuric acid is also employed in the nitration step.

4. The process of claim 1 wherein the hydrolyzing agent is a lower alkanol.

5. The process of claim 4 wherein the lower alkanol is methanol.

6. The process of claim 1 wherein 4,6-diamino-1,3-benzenediol is recovered in a purity of at least 99 weight percent.

7. The process of claim 1 wherein 4,6-diamino-1,3-benzenediol is recovered in a purity of at least 99.9 weight percent.

8. The process of claim 3 wherein the molar ratio of concentrated nitric acid to the 1,3-bis(alkylcarbonato)benzene is in the range of about 2:1 to about 3.3:1, the molar ratio of sulfuric acid to the 1,3-bis(alkylcarbonato)benzene is in the range from about 9.5:1 to about 20:1 and the temperature in step (a) is in the range from about −5° C. to about 40° C.

9. The process of claim 5 wherein the molar ratio of methanol to the 1,3-bis(alkylcarbonato)nitrobenzene is in the range from about 5:1 to about 100:1 and the temperature in step (b) is in the range from about 20° C. to about 100° C.

10. The process of claim 1 wherein the mole ratio of hydrogen gas to the nitro-1,3-benzenediol is in the range from about 6:1 to about 20:1, the molar equivalent ratio of the hydrogenation catalyst to nitro-1,3-benzenediol is in the range from about 0.001:1 to about 1:1 and the temperature used in step (c) is from about 0° C. to about 150° C.

11. The process of claim 1 wherein the nitro-1,3-benzenediol is 4-nitro-1,3-benzenediol and the amino-1,3-benzenediol is 4-amino-1,3-benzenediol.

12. The process of claim 1 wherein the nitro-1,3-benzenediol is 2-methyl-4,6-dinitro-1,3-benzenediol and the amino-1,3-benzenediol is 2-methyl-4,6-diamino-1,3-benzenediol.

* * * * *